(12) United States Patent
Mahajan et al.

(10) Patent No.: US 11,289,202 B2
(45) Date of Patent: Mar. 29, 2022

(54) METHOD AND SYSTEM TO IMPROVE CLINICAL WORKFLOW

(71) Applicant: Cardiac Pacemakers, Inc., St. Paul, MN (US)

(72) Inventors: Deepa Mahajan, North Oaks, MN (US); Bhaskar Sen, St. Paul, MN (US); Sunipa Saha, Shoreview, MN (US); David L. Perschbacher, Coon Rapids, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 546 days.

(21) Appl. No.: 16/212,155

(22) Filed: Dec. 6, 2018

(65) Prior Publication Data

US 2019/0172583 A1 Jun. 6, 2019

Related U.S. Application Data

(60) Provisional application No. 62/595,482, filed on Dec. 6, 2017.

(51) Int. Cl.
*G16H 50/20* (2018.01)
*G06N 20/00* (2019.01)
(Continued)

(52) U.S. Cl.
CPC ........... *G16H 50/20* (2018.01); *A61B 5/0245* (2013.01); *A61B 5/361* (2021.01); *A61B 5/7267* (2013.01); *A61N 1/37258* (2013.01);

*G06N 20/00* (2019.01); *G16H 10/60* (2018.01); *G16H 50/30* (2018.01); *G16H 50/70* (2018.01); *A61B 5/0006* (2013.01)

(58) Field of Classification Search
None
See application file for complete search history.

(56) References Cited

U.S. PATENT DOCUMENTS

2003/0154181 A1* 8/2003 Liu ................. G06K 9/6226
2008/0071182 A1 3/2008 Cazares et al.
(Continued)

FOREIGN PATENT DOCUMENTS

CN 111684539 A 9/2020
EP 1066083 A1 * 1/2001 ............ G16H 40/63
(Continued)

OTHER PUBLICATIONS

Manning et al., Introduction to Information Retrieval, 2009, Cambridge University Press, Section 16, https://nlp.stanford.edu/IR-book/pdf/irbookonlinereading.pdf (Year: 2009).*
(Continued)

*Primary Examiner* — Devin C Hein
(74) *Attorney, Agent, or Firm* — Schwegman Lundberg & Woessner, P.A.

(57) ABSTRACT

Described herein are systems and methods for classifying clinical episodes in order to more accurately generate alerts for those episodes that warrant them. In some embodiments, alerts are only generated for those episodes that are new or different from previous episodes, where the previous episodes have been found to be not significant enough to warrant an alert.

17 Claims, 5 Drawing Sheets

(51) Int. Cl.
*G16H 50/30* (2018.01)
*G16H 10/60* (2018.01)
*G16H 50/70* (2018.01)
*A61B 5/00* (2006.01)
*A61B 5/0245* (2006.01)
*A61N 1/372* (2006.01)
*A61B 5/361* (2021.01)

(56) References Cited

U.S. PATENT DOCUMENTS

| | | | | |
|---|---|---|---|---|
| 2013/0111509 | A1* | 5/2013 | Guo | H04H 60/65 |
| | | | | 725/12 |
| 2015/0356252 | A1 | 12/2015 | Beker | |
| 2016/0081566 | A1* | 3/2016 | Xu | A61B 5/1102 |
| | | | | 600/450 |
| 2016/0364467 | A1* | 12/2016 | Gupta | G06N 20/00 |
| 2017/0154280 | A1* | 6/2017 | Adir | G06F 16/906 |

FOREIGN PATENT DOCUMENTS

| | | |
|---|---|---|
| EP | 1066083 A1 | 1/2001 |
| EP | 1609412 A1 | 12/2005 |
| WO | WO-2010111895 A1 | 10/2010 |
| WO | WO-2019113323 A1 | 6/2019 |

OTHER PUBLICATIONS

Amorim et al., Clustering Stability and Ground Truth: Numerical Experiments, 2015, 7th International Joint Conference on Knowledge Discovery, Knowledge Engineering and Knowledge Management (IC3K), https://ieeexplore.ieee.org/document/7526928/references#references , (Year: 2015).*

Kodinariya et al., Review on determining number of Cluster in K-Means Clustering, 20163, International Journal of Advance Research in Computer Science and Management Studies, vol. 1, Issue 6, ISSN: 2321-7782 (Online), (Year: 2013).*

"European Application Serial No. 18821975.2, Response filed Feb. 5, 2021 to Communication pursuant to Rules 161(10 and 162 EPC dated Jul. 28, 2020", 16 pgs.

"International Application Serial No. PCT/US2018/064260, International Preliminary Report on Patentability dated Jun. 18, 2020", 17 pgs.

"International Application Serial No. PCT/US2018/064260, International Search Report dated Mar. 7, 2019", 6 pgs.

"International Application Serial No. PCT/US2018/064260, Written Opinion dated Mar. 7, 2019", 15 pgs.

Haldar, Nur Al Hasan, et al., "Arrhythmia classification using Mahalanobis distance based improved Fuzzy C-Means clustering for mobile health monitoring system", NEUROCOMPUTING vol. 220, 221-235.

* cited by examiner

METHOD AND SYSTEM TO IMPROVE CLINICAL WORKFLOW

CLAIM OF PRIORITY

This application claims the benefit of priority under 35 U.S.C. § 119(e) of U.S. Provisional Patent Application Ser. No. 62/595,482, filed on Dec. 6, 2017, which is herein incorporated by reference in its entirety.

TECHNICAL FIELD

This document relates generally to medical methods and devices, and more particularly, but not by way of limitation, to systems, devices, and methods to monitor and evaluate clinical data.

BACKGROUND

Clinical personnel, in taking care of hospitalized patients, need to respond to alerts, either generated by the patients or by instrumentation, that indicate some attention to the patient may be required. Examples of instrumentation-type alerts include when the equipment detects the presence of a cardiac arrhythmia such as atrial fibrillation. The quantity of alerts for a specific clinic, however, can sometimes overwhelm the human resources required to review the alerts. The majority of alerts are limited to repeating alerts from a small percentage of a clinic's patients. These alerts must continue to be reviewed, however, in case something changes. Examples of situations where a review may be necessary include: if a true-positive occurs for a patient with frequent false positives, if an extreme true-positive occurs for a patient with frequent true positives, or if a patient who pushes the patient-activated-trigger every day because they feel bad now pushes it during an actual arrhythmia. There is thus a need for methods and devices to automatically identify different and/or new types of clinical episodes for a patient so that the clinical staff is only presented with alerts for such new or different episodes.

SUMMARY

This document discusses, among other things, systems and methods to classify collected clinical data in order to improve clinical workflow.

In Example 1, a computer-implemented method comprises: accepting input data relating to past clinical episodes collected from a patient over time, grouping the past clinical episodes into one or more classification clusters accordance with a similarity metric; receiving additional input data relating to a new clinical episode collected from the patient; assigning the new clinical episode to a classification cluster if the new clinical episode is similar to one or more of the past clinical episode contained within the classification cluster as determined the similarity metric; and, issuing an alert or displaying the new clinical episode on a display if the new clinical episode is not assigned to a classification cluster.

In Example 2, the subject matter of Example 1 or any of the Examples herein may optionally include: wherein each past clinical episode is represented by a past episode vector in a p-dimensional vector space made up of p numerically valued features reflective of the patient's clinical condition, p being an integer; and further comprising: applying a clustering procedure to the past episode vectors to compute clusters that groups the past episode vectors into a plurality of clusters based upon a distance metric in the p-dimensional vector space; defining the one or more classification clusters as represented by the centroids of clusters of past episode vectors generated by the clustering procedure; and, assigning a new episode vector representing a recent clinical episode to the classification cluster that corresponds to the centroid closest to the new episode vector if the distance from the new episode vector to the closest centroid of a classification cluster is less than a specified value.

In Example 3, the subject matter of Example 2 or any of the Examples herein may optionally include: designating one or more of the classification clusters as clinically significant so as to warrant an alert; and, if the new episode vector is assigned to a clinically significant classification cluster, issuing an alert.

In Example 4, the subject matter of Example 2 or any of the Examples herein may optionally include wherein the distance metric in the p-dimensional vector space is a Euclidean distance, a squared Euclidean distance, a Minkowski distance, a Manhattan distance, a Pearson correlation distance, a Pearson squared distance, a Chebyshev distance, or a Spearman distance.

In Example 5, the subject matter of Example 2 or any of the Examples herein may optionally include, if a new episode vector is not assigned to a classification cluster, classifying the recent clinical episode represented by that new episode vector as dissimilar to past clinical episodes.

In Example 6, the subject matter of Example 2 or any of the Examples herein may optionally include issuing an alert if a recent clinical episode is classified dissimilar to past clinical episodes in accordance with a specified value of the distance metric.

In Example 7, the subject matter of Example 2 or any of the Examples herein may optionally include: 1) selecting some or all of the past episode vectors as a training set and dividing the training set into a training subset and a pseudo-validation subset; 2) performing the clustering procedure on the training subset and computing an optimal number of clusters as part of the clustering procedure; 3) assigning vectors of the pseudo-validation subset to the clusters of the training subset in a manner that minimizes the distance from the pseudo-validation subset vector to the centroid of the cluster to which it is assigned; 4) performing the clustering procedure on the pseudo-validation subset, wherein the number of clusters to be computed is specified to be the same as the optimal number of clusters computed as part of the clustering procedure applied to the training subset; 5) evaluating the accuracy of the clusters of the training subset to which the pseudo-validation subset vectors are assigned in classifying those vectors using the clusters computed as a result of applying the clustering procedure to the pseudo-validation subset as a ground-truth standard; 6) after re-dividing the training set into different training and pseudo-validation subsets, iteratively performing 2) through 5) a specified number of times; and, 7) selecting the centroids of the clusters of the training subset that are evaluated with the highest accuracy to represent the classification clusters.

In Example 8, the subject matter of Example 7 or any of the Examples herein may optionally include testing the accuracy of the classification clusters in classifying vectors by: selecting some or all of the past episode vectors not selected as the training set to be a test set; assigning vectors of the test set to the classification clusters in a manner that minimizes the distance from the test set vector to the centroid of the cluster to which it is assigned; performing the clustering procedure on the test set, wherein the number of clusters to be computed is specified to be the same as the number of classification clusters; and, evaluating the accuracy of the classification clusters to which the test vectors have been assigned in classifying the test vectors using the clusters computed by applying the clustering procedure to the test set as a ground-truth standard.

In Example 9, the subject matter of Example 7 or any of the Examples herein may optionally include, after a specified period time or after a specified number of new episode vectors have been collected, adding the collected new episode vectors to the past episode vectors and re-computing the classification clusters.

In Example 10, the subject matter of Example 7 or any of the Examples herein may optionally include weighting newer past episode vectors more heavily than older past episode vectors in computing the classification clusters.

In Example 11, the subject matter of Example 2 or any of the Examples herein may optionally include incorporating patient or clinician feedback in computing the classification clusters by assigning past clinical episode vectors to a particular classification cluster in accordance with the feedback.

In Example 12, the subject matter of Example 2 or any of the Examples herein may optionally include wherein the clustering procedure is a K-means algorithm performed by: 1) assigning the past episode vectors as belonging to one of K clusters, where K is an integer, and calculating the coordinates in the p-dimensional vector space of the centroid of each of the K clusters as the average of the feature values of the past episode vectors belonging to the cluster; 2) re-assigning each of the past episode vectors to the one of the K clusters whose centroid is closest to the past episode vector; 3) calculate the coordinates of the centroid of each of the K clusters as the average of the feature values of the past episode vectors belonging to the cluster; and, 4) iteratively performing 2) through 3) until a specified termination condition is met.

In Example 13, the subject matter of Example 12 or any of the Examples herein may optionally include wherein the specified termination condition is selected from: a specified number of iterations having been performed, the coordinates of the centroid of each of the K clusters not changing between iterations, and the sum of the squared distances from each past episode vector to the centroid of the cluster to which it has been assigned being below a specified threshold value.

In Example 14, the subject matter of Example 12 or any of the Examples herein may optionally include calculating an optimal value for the number of clusters K by: computing clusters using the K-means clustering procedure for successively increasing values of K; for each set clusters computed using a particular K value, computing a dispersion function defined as the sum of the squared distances between a centroid of a cluster and the vectors belonging to the cluster summed over all of the clusters in the set; and, selecting the optimal value of K as the K value when the marginal decrease in the dispersion function as K is increased is maximized.

In Example 15, the subject matter of Example 8 or any of the Examples herein may optionally include wherein the accuracy of clusters in classifying vectors is evaluated as being positively related to a mutual information MI between the set of clusters to be evaluated {w(1), w(2), . . . w(N) and the set of clusters regarded as ground truth {c(1), c(2), . . . c(N), where w(k) is the set of vectors in cluster k of the set of clusters to be evaluated, c(j) is the set of vectors in cluster j of the set of clusters regarded as ground truth, N is the number of clusters in the set of clusters to be evaluated and the set of clusters regarded as ground truth, and wherein MI is calculated as:

$$MI = \sum_{k}^{N} \sum_{j}^{N} P(w(k) \cap c(j)) \log \frac{P(w(k) \cap c(j))}{P(w(k))P(c(k))}$$

where $P(w(k))$, $P(c(j))$, and $P(w(k) \cap c(j))$ are the probabilities of a vector being in $w(k)$, $c(j)$, and the intersection of $w(k)$ and $c(j)$, respectively, estimated as the relative frequencies of the vectors in the clusters to be evaluated and the clusters regarded as ground truth.

In Example 16, the subject matter of Example 1 or any of the Examples herein may optionally include wherein the features of the past or new episode vectors include features related to cardiac arrhythmias such as atrial fibrillation.

In Example 17, the subject matter of Example 1 or any of the Examples herein may optionally include wherein the features of the past or new episode vectors include physiological sensor measurements or numerical values calculated or otherwise derived therefrom.

In Example 18, the subject matter of Example 1 or any of the Examples herein may optionally include wherein the features of the past or new episode vectors include numerical values corresponding to clinician input based upon patient observation.

In Example 19, the subject matter of Example 1 or any of the Examples herein may optionally include wherein the features of the past or new episode vectors include features collected by an implantable or wearable medical device.

In Example 20, the subject matter of Example 1 or any of the Examples herein may optionally include wherein the features of the past or new episode vectors include features collected by a cardiac rhythm management device.

In Example 21, a computing device comprises: processing circuitry and memory; wherein the processing circuitry is configured to: accept input data relating to past clinical episodes collected from a patient over time; group the past clinical episodes into one or more classification clusters accordance with a similarity metric; receive additional input data relating to a new clinical episode collected from the patient; assign the new clinical episode to a classification cluster if the new clinical episode is similar to one or more of the past clinical episode contained within the classification cluster as determined the similarity metric; and, issue an alert or display the new clinical episode on a display if the new clinical episode is not assigned to a classification cluster.

In Example 22, the subject matter of Example 21 or any of the Examples herein may optionally include wherein past and new clinical episodes are represented by an episode vector in a p-dimensional vector space made up of p numerically valued features reflective of the patient's clinical condition, p being an integer and wherein the processing circuitry is further configured to: apply a clustering procedure to the past episode vectors to compute clusters that groups the past episode vectors into a plurality of clusters based upon a distance metric in the p-dimensional vector space; and, define the one or more classification clusters as represented by the centroids of clusters of past episode vectors generated by the clustering procedure; and, assign a new episode vector representing a recent clinical episode to the classification cluster that corresponds to the centroid closest to the new episode vector if the distance from the new episode vector to the closest centroid of a classification cluster is less than a specified value.

In Example 23, the subject matter of Example 22 or any of the Examples herein may optionally include: wherein the processing circuitry is further to: designate one or more of the classification clusters as clinically significant so as to warrant an alert; and, if the new episode vector is assigned to a clinically significant classification cluster, issue an alert.

In Example 24, the subject matter of Example 22 or any of the Examples herein may optionally include wherein the distance metric in the p-dimensional vector space is a Euclidean distance, a squared Euclidean distance, a Minkowski distance, a Manhattan distance, a Pearson correlation distance, a Pearson squared distance, a Chebyshev distance, or a Spearman distance.

In Example 25, the subject matter of Example 22 or any of the Examples herein may optionally include: wherein the processing circuitry is further to, if a new episode vector is not assigned to a classification cluster, classify the recent clinical episode represented by that new episode vector as dissimilar to past clinical episodes.

In Example 26, the subject matter of Example 22 or any of the Examples herein may optionally include wherein the processing circuitry is further to issue an alert if a recent clinical episode is classified dissimilar to past clinical episodes in accordance with a specified value of the distance metric.

In Example 27, the subject matter of Example 22 or any of the Examples herein may optionally include: wherein the processing circuitry is further to: 1) select some or all of the past episode vectors as a training set and divide the training set into a training subset and a pseudo-validation subset; 2) perform the clustering procedure on the training subset and computing an optimal number of clusters as part of the clustering procedure; 3) assign vectors of the pseudo-validation subset to the clusters of the training subset in a manner that minimizes the distance from the pseudo-validation subset vector to the centroid of the cluster to which it is assigned; 4) perform the clustering procedure on the pseudo-validation subset, wherein the number of clusters to be computed is specified to be the same as the optimal number of clusters computed as part of the clustering procedure applied to the training subset; 5) evaluate the accuracy of the clusters of the training subset to which the pseudo-validation subset vectors are assigned in classifying those vectors using the clusters computed as a result of applying the clustering procedure to the pseudo-validation subset as a ground-truth standard; 6) after re-dividing the training set into different training and pseudo-validation subsets, iteratively perform 2) through 5) a specified number of times; and, 7) select the centroids of the clusters of the training subset that are evaluated with the highest accuracy to represent the classification clusters.

In Example 28, the subject matter of Example 22 or any of the Examples herein may optionally include wherein the processing circuitry is further to test the accuracy of the classification clusters in classifying vectors by: selecting some or all of the past episode vectors not selected as the training set to be a test set; assigning vectors of the test set to the classification clusters in a manner that minimizes the distance from the test set vector to the centroid of the cluster to which it is assigned; performing the clustering procedure on the test set, wherein the number of clusters to be computed is specified to be the same as the number of classification clusters; and, evaluating the accuracy of the classification clusters to which the test vectors have been assigned in classifying the test vectors using the clusters computed by applying the clustering procedure to the test set as a ground-truth standard.

In Example 29, the subject matter of Example 22 or any of the Examples herein may optionally include wherein the processing circuitry is further to, after a specified period time or after a specified number of new episode vectors have been collected, add the collected new episode vectors to the past episode vectors and re-compute the classification clusters.

In Example 30, the subject matter of Example 29 or any of the Examples herein may optionally include wherein the processing circuitry is further to weight newer past episode vectors more heavily than older past episode vectors in computing the classification clusters.

In Example 31, the subject matter of Example 22 or any of the Examples herein may optionally include: a user interface and wherein the processing circuitry is further to incorporate patient or clinician feedback in computing the classification clusters by assigning past clinical episode vectors to a particular classification cluster in accordance with the feedback.

In Example 32, the subject matter of Example 22 or any of the Examples herein may optionally include wherein the clustering procedure is a K-means algorithm performed by: 1) assigning the past episode vectors as belonging to one of K clusters, where K is an integer, and calculating the coordinates in the p-dimensional vector space of the centroid of each of the K clusters as the average of the feature values of the past episode vectors belonging to the cluster; 2) re-assigning each of the past episode vectors to the one of the K clusters whose centroid is closest to the past episode vector; 3) calculate the coordinates of the centroid of each of the K clusters as the average of the feature values of the past episode vectors belonging to the cluster; and, 4) iteratively performing 2) through 3) until a specified termination condition is met.

In Example 33, the subject matter of Example 22 or any of the Examples herein may optionally include wherein the specified termination condition is selected from: a specified number of iterations having been performed, the coordinates of the centroid of each of the K clusters not changing between iterations, and the sum of the squared distances from each past episode vector to the centroid of the cluster to which it has been assigned being below a specified threshold value.

In Example 34, the subject matter of Example 22 or any of the Examples herein may optionally include wherein the processing circuitry is further to calculate an optimal value for the number of clusters K by: computing clusters using the K-means clustering procedure for successively increasing values of K; for each set clusters computed using a particular K value, computing a dispersion function defined as the sum of the squared distances between a centroid of a cluster and the vectors belonging to the cluster summed over all of the clusters in the set; and, selecting the optimal value of K as the K value when the marginal decrease in the dispersion function as K is increased is maximized.

In Example 35, the subject matter of Example 22 or any of the Examples herein may optionally include wherein the accuracy of clusters in classifying vectors is evaluated as being positively related to a mutual information MI between the set of clusters to be evaluated $\{w(1), w(2) \ldots w(N)\}$ and the set of clusters regarded as ground truth $\{c(1), c(2), \ldots c(N)\}$, where $w(k)$ is the set of vectors in cluster k of the set of clusters to be evaluated, $c(j)$ is the set of vectors in cluster j of the set of clusters regarded as ground truth, N is the number of clusters in the set of clusters to be evaluated and the set of clusters regarded as ground truth, and wherein MI is calculated as:

$$MI = \sum_{k}^{N} \sum_{j}^{N} P(w(k) \cap c(j)) \log \frac{P(w(k) \cap c(j))}{P(w(k))P(c(k))}$$

where $P(w(k))$, $P(c(j))$, and $P(w(k) \cap c(j))$ are the probabilities of a vector being in $w(k)$, $c(j)$, and the intersection of $w(k)$ and $c(j)$, respectively, estimated as the relative frequencies of the vectors in the clusters to be evaluated and the clusters regarded as ground truth.

In Example 36, the subject matter of Example 22 or any of the Examples herein may optionally include wherein the features of the past or new episode vectors include features related to cardiac arrhythmias.

In Example 37, the subject matter of Example 22 or any of the Examples herein may optionally include: one or more physiological sensors interfaced to the processing circuitry and wherein the features of the past or new episode vectors include physiological sensor measurements or numerical values calculated or otherwise derived therefrom.

In Example 38, the subject matter of Example 22 or any of the Examples herein may optionally include: a user interface and wherein the processing circuitry is further to collect features of the past or new episode vectors that include numerical values corresponding to clinician input based upon patient observation.

In Example 39, the subject matter of Example 22 or any of the Examples herein may optionally include: a telemetry unit interfaced to the processing circuitry for communicating with a wearable or implantable medical device and wherein the processing circuitry is further to collect features of the past or new episode vectors that include features collected by the implantable or wearable medical device.

In Example 40, the subject matter of Example 39 or any of the Examples herein may optionally include wherein the features of the past or new episode vectors include features collected by a cardiac rhythm management device.

In Example 41, the subject matter of Example 22 or any of the Examples herein may optionally include wherein the device is incorporated into an implantable or wearable medical device.

Example 42 is a computer-readable storage medium that comprises instructions to cause processing circuitry of a computing device, upon execution of the instructions by the processing circuitry, to perform any of the methods recited by Examples 1 through 20.

Example 43 comprises means for performing any of the methods recited by Examples 1 through 20.

This summary is intended to provide an overview of subject matter of the present patent application. It is not intended to provide an exclusive or exhaustive explanation of the disclosure. The detailed description is included to provide further information about the present patent application. Other aspects of the disclosure will be apparent to persons skilled in the art upon reading and understanding the following detailed description and viewing the drawings that form a part thereof, each of which are not to be taken in a limiting sense.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
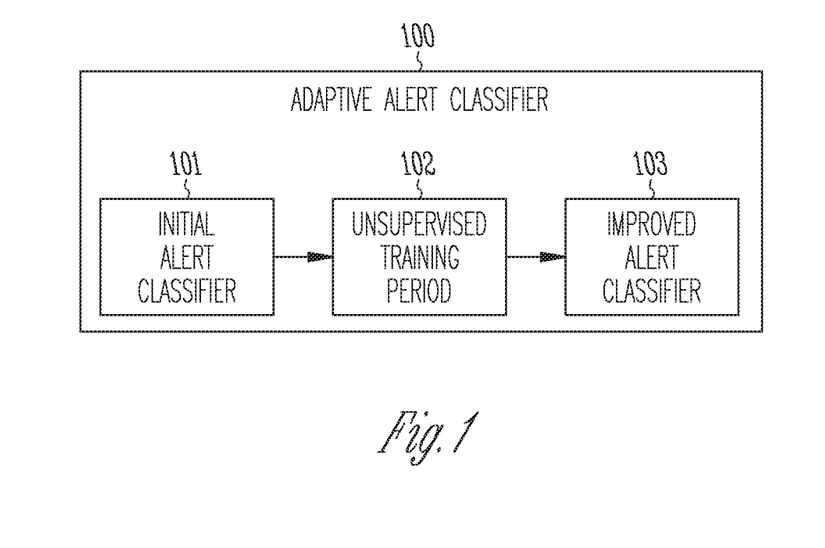
FIG. 1 illustrates a general approach to decision making for improving clinical workflow in accordance with some embodiments.

Described herein are systems and methods for classifying clinical episodes in order to more accurately generate alerts for those episodes that warrant them. In some embodiments, alerts are only generated for those episodes that are new or different from previous episodes, where the previous episodes have been found to be not significant enough to warrant an alert. FIG. 1 illustrates a general approach in accordance with some embodiments. An adaptive alert classifier 100 operates as an initial alert classifier 101, undergoes an unsupervised training period 102, and then operates as an improved alert classifier 103. During the unsupervised training period, the alert classifier learns to identify the characteristics of those episodes that warrant issuing an alert and those that do not.

In some embodiments, data relating to past clinical episodes is collected from a patient over time, wherein each past clinical episode is represented by a past episode vector in a p-dimensional vector space made up of p numerically valued features reflective of the patient's clinical condition, p being an integer. The past clinical episodes are then grouped into one or more classification clusters in accordance with a similarity metric. These classification clusters are then used to classify future collected data by assigning a new episode vector representing a recent clinical episode to a classification cluster if the new episode vector is similar enough to the past clinical episode vectors contained within the classification cluster as determined by a specified threshold value of the similarity metric. An alert may be issued if the new episode vector is not assigned to a classification cluster and/or if the new episode vector is assigned to a classification cluster deemed to be clinically significant.

In some embodiments, the grouping of the past episode vectors is performed by applying a clustering procedure to the past episode vectors. Different types of clustering procedures or algorithms may be used for this purpose including: 1) centroid-based clustering where clusters are represented by a central vector that is not necessarily a member of the data set, 2) distribution-based clustering based upon distribution models, 3) density-based clustering where clusters are defined as areas of higher density than the remainder of the data set, and 4) connectivity-based clustering (a.k.a.

hierarchical clustering) where clusters are defined primarily by the maximum distance needed to connect parts of the cluster. In certain examples discussed herein, a type of centroid-based clustering procedure, k-means, is applied to cluster the past episodes based upon a distance metric in vector space. This should not be regarded as limiting, however, as other clustering procedures such as those described above could be employed.

In some embodiments, the clustering procedure computes clusters that groups the past episode vectors into a plurality of clusters based upon a distance metric in the p-dimensional vector space and defines the one or more classification clusters as represented by the centroids of those clusters. The distance metric in the p-dimensional vector space may be, for example, a Euclidean distance, a squared Euclidean distance, a Minkowski distance, a Manhattan distance, a Pearson correlation distance, a Pearson squared distance, a Chebyshev distance, or a Spearman distance. A new episode vector representing a recent clinical episode may then be assigned to the classification cluster that corresponds to the centroid closest to the new episode vector if the distance from the new episode vector to the closest centroid of a classification cluster is less than a specified value. If a new episode vector is not assigned to a classification cluster, the recent clinical episode represented by that new episode vector may be regarded as dissimilar to any of the past clinical episodes, and amount of dissimilarity may be quantified as the distance of the new episode vector to its closest centroid.

Figure 2:
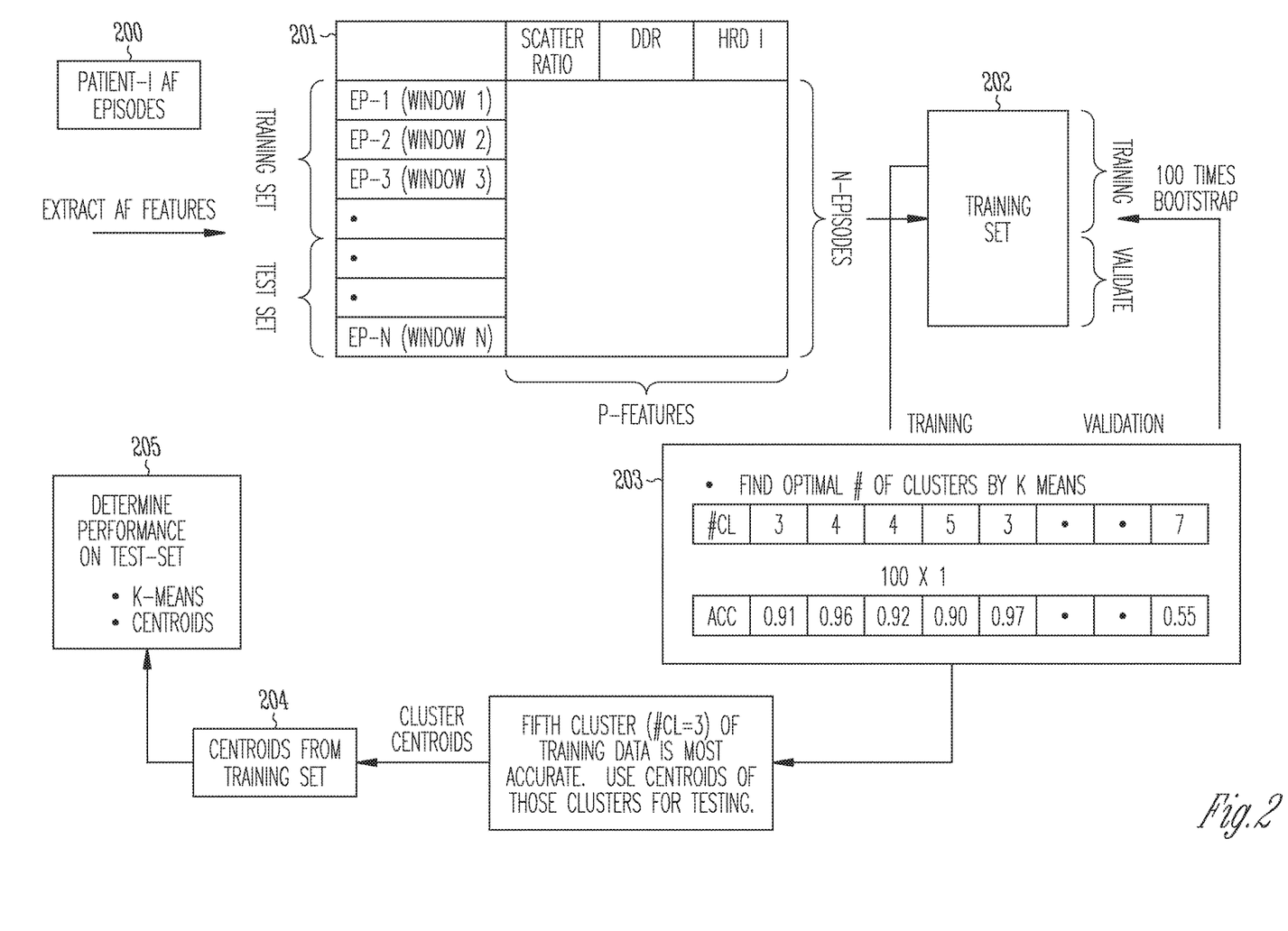
FIG. 2 illustrates an overview of the data flow in a procedure for computing classification clusters in accordance with some embodiments.

FIG. 2 illustrates an overview of the procedure for computing classification clusters in accordance with one embodiment in which the clinical episodes are episodes of atrial fibrillation (AF) 200, each of which is represented by a plurality of extracted features. The past clinical episodes are each represented by a past episode vector in a p-dimensional vector space made up of p numerically valued features reflective of the patient's clinical condition. The features of the past episode vectors in this example may include such things as heart rate, heart rate variability, heart rate density index, and other parameters derived from electrocardiographic data that pertain to AF. A collection 201 of N such past episode vectors is shown in the figure where. The collection 201 may be divided into a training set 202 and a test set. As will be described in more detail below, the training set 202 may be used to in a machine learning algorithm to compute the classification clusters for classifying episode vectors collected in the future as clinically significant or not. In one embodiment, a k-means clustering procedure is applied to the training set 202 in order to group the episode vectors into a plurality of clusters with each cluster represented by a centroid in the p-dimensional vector space. The clustering procedure may be performed iteratively on different subgroupings of the training set divided into a training subset and a pseudo-validation subset in order to determine optimal number of clusters and the cluster centroids. In this particular example, the procedure is performed 100 times with the training set shuffled between iterations into a different training subset and a pseudo-validation subset. The results of the iterations are collected as a record 203 that contains the optimal number of clusters and centroid locations computed by each of the 100 iterations of the clustering procedure along a calculated accuracy of the clusters for each iteration. As shown in the figure for this particular example, the fifth clustering iteration, where the optimum number clusters is computed to be three, is found to have an accuracy of 97 percent and is the most accurate. The cluster centroids of that iteration may then be collected as data 204 to be used to determine the performance of the clusters in classifying the vectors of the test set at stage 205.

Figure 3:
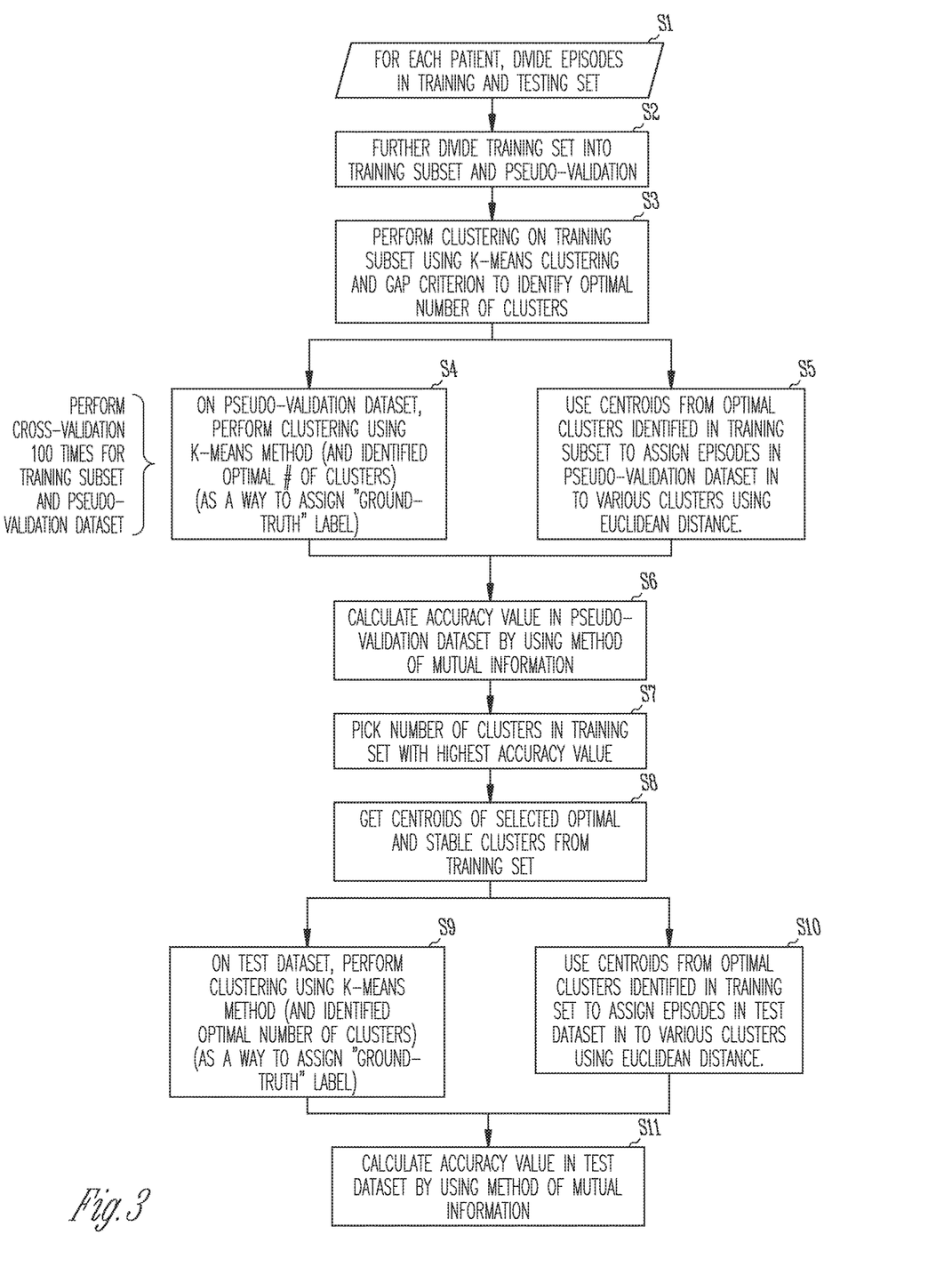
FIG. 3 illustrates the stages involved in computing and testing classification clusters in accordance with some embodiments.

A more detailed description of the procedures for computing classification clusters in some embodiments is as follows with reference to FIG. 3. At stage S1, for each patient, a collection of past episode vectors is obtained. Some or all of the past episode vectors are selected as a training set and then divided into a training subset and a pseudo-validation subset at stage S2. The clustering procedure is then performed on the training subset at stage S3, where an optimal number of clusters is also computed as part of the clustering procedure. A number of clustering algorithms may be used to cluster the training subset. In one example, the clustering procedure is a K-means algorithm that assigns the past episode vectors as belonging to one of K clusters, where K is an integer, and calculates the coordinates in the p-dimensional vector space of the centroid of each of the K clusters as the average of the feature values of the past episode vectors belonging to the cluster. Each of the past episode vectors is then reassigned to the one of the K clusters whose centroid is closest to the past episode vector, and the coordinates of the centroid of each of the K clusters is calculated as the average of the feature values of the past episode vectors belonging to the cluster. The steps are performed iteratively until a specified termination condition is met. The specified termination condition may be selected from: a specified number of iterations having been performed, the coordinates of the centroid of each of the K clusters not changing between iterations, and the sum of the squared distances from each past episode vector to the centroid of the cluster to which it has been assigned being below a specified threshold value. An optimal value for the number of clusters K may be computed by the so-called GAP criterion where clusters are computed using the K-means clustering procedure for successively increasing values of K. For each set clusters computed using a particular K value, a dispersion function defined as the sum of the squared distances between a centroid of a cluster and the vectors belonging to the cluster summed over all of the clusters in the set is computed. The optimal value of K may then be selected as the K value when the marginal decrease in the dispersion function as K is increased is maximized.

At stages S4 through S6, the clustering procedure is performed on the training subset with cross validation using the pseudo-validation subset in iterative fashion for some specified number of times (e.g., 100 times), where the training set is shuffled into different combinations for the training subset and pseudo-validation subset between iterations. After each iteration of the clustering procedure, vectors of the pseudo-validation subset are assigned at stage S5 to the clusters of the training subset computed by the clustering procedure in a manner that minimizes the distance from the pseudo-validation subset vector to the centroid of the cluster to which it is assigned. The clustering procedure is then performed on the pseudo-validation subset at stage S4, where the number of clusters to be computed is specified to be the same as the optimal number of clusters computed as part of the clustering procedure applied to the training subset. The accuracy of the clusters of the training subset to which the pseudo-validation subset vectors are assigned in classifying those vectors may then be determined using the clusters computed as a result of applying the clustering procedure to the pseudo-validation subset as a ground-truth standard at stage S6. After re-dividing the training set into different training and pseudo-validation subsets, and performance of the clustering and cross validation procedures for a specified number of times, the centroids of the clusters of the training subset that are evaluated with the highest accuracy at stage S7 may be selected at stage S8 to represent the classification clusters.

After computation of the classification clusters as described above, the accuracy of the classification clusters in classifying vectors may be evaluated by applying the clusters to classify members of the past episode vectors selected as a test set. Note that the vectors of the test set were not used to compute the classification clusters as described above. Stages S9 through S11 are basically similar to stages S4 through S6 as described above except applied to the training set and test set instead of the training subset and pseudo-validation subset. That is, some or all of the past episode vectors not selected as the training set are selected to be a test set. Vectors of the test set are then assigned to the classification clusters in a manner that minimizes the distance from the test set vector to the centroid of the cluster to which it is assigned. The clustering procedure is then performed on the test set, wherein the number of clusters to be computed is specified to be the same as the number of classification clusters. The accuracy of the classification clusters to which the test vectors have been assigned in classifying the test vectors may then be evaluated using the clusters computed by applying the clustering procedure to the test set as a ground-truth standard.

There are a number of different ways to evaluate the accuracy of classification clusters at stages S6 or S11. In one embodiment, the method of mutual information (MI) is used. In this method, the accuracy of classification clusters in classifying vectors is evaluated as being positively related to a mutual information MI between the set of clusters to be evaluated $\{w(1), w(2), \ldots w(N)$ and the set of clusters regarded as ground truth $\{c(1), c(2), \ldots c(N)$. The set $w(k)$ is the set of vectors in cluster k of the set of clusters to be evaluated, $c(j)$ is the set of vectors in cluster j of the set of clusters regarded as ground truth, N is the number of clusters in the set of clusters to be evaluated and the set of clusters regarded as ground truth. The mutual information MI may then be calculated as:

$$MI = \sum_k^N \sum_j^N P(w(k) \cap c(j)) \log \frac{P(w(k) \cap c(j))}{P(w(k))P(c(k))}$$

where $P(w(k))$, $P(c(j))$, and $P(w(k) \cap c(j))$ are the probabilities of a vector being in $w(k)$, $c(i)$, and the intersection of $w(k)$ and $c(j)$, respectively, estimated as the relative frequencies of the vectors in the clusters to be evaluated and the clusters regarded as ground truth.

In some embodiments, classification clusters may be re-computed in the manner described above after a specified period of time or after a specified number of new episode vectors have been collected. For the re-computation, newly collected new episode vectors may be added to the past episode vectors, and older past episode vectors may be removed. The newer past episode vectors may weighted more heavily than older past episode vectors in computing the classification clusters. That is, the centroid locations of the computed clusters may be made more dependent upon newer past episode vectors than older ones. Also, patient or clinician feedback may be incorporated in computing the classification clusters by assigning past clinical episode vectors to a particular classification cluster in accordance with the feedback.

Figure 4:
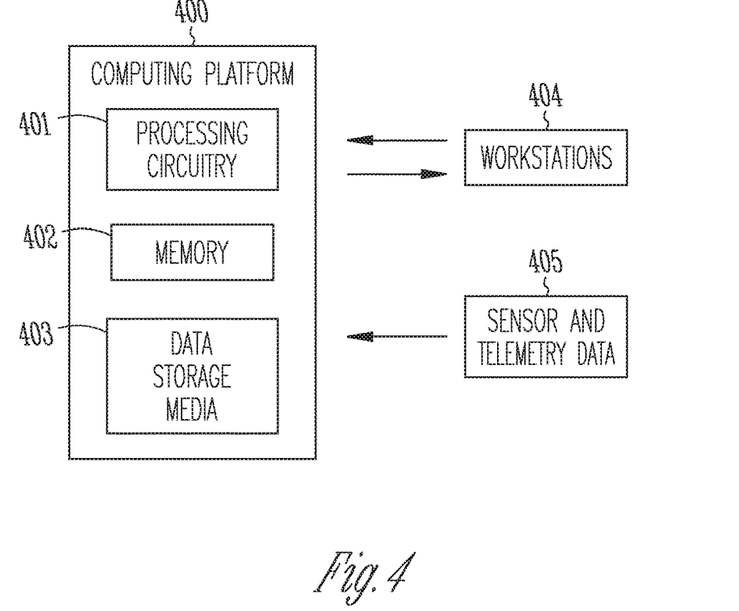
FIG. 4 illustrates a computing platform for performing the procedures described herein in accordance with some embodiments.

The procedures described above for classifying clinical data and issuing alerts may be implemented in a number of different embodiments of a computing device. In one embodiment as illustrated by FIG. 4, a computing platform 400 is a server having processing circuitry 401, memory 402, and data storage media 403. The platform 400 is programmed to process clinical episode data that may be either entered manually by clinical personnel via workstations 404 or directly input to the platform via sensor connections or telemetry 405. For example, electrocardiographic and other patient data may be communicated to the platform via bedside instrumentation or telemetered to the platform via telemetry interface from implantable or wearable devices such as Holter monitors and cardiac rhythm management devices. The computing platform may then perform the data classification procedures and issue alerts to workstations 403. In some embodiments, the computing platform 401 may communicate with a cloud computing platform via network interface 405 that may perform some or all of the data classification computing.

When an alert is issued, it may be displayed on a display of the workstation 404. Data relating to new episodes, whether or not they result in an alert, may also be displayed. Data relating to a plurality of new or past episodes may also be displayed. Multiple new or past episodes may also be displayed and sorted, prioritized, or grouped on the display according to the cluster or similarity metric. Also, when an alert is issued and a data relating to the new episode causing the alert is displayed, more or less information may be displayed with the alert depending on the clustering. For example, for a new episode that is more dissimilar by some specified criterion to past episodes as represented by the classification clusters, more data may be provided (such as egrams, trends, etc.) along with the alert than for a new episode that does not meet the specified dissimilarity criterion. Also, the similarity metric or some other similarity indicator may also be displayed with the alerts. Input to the workstation may also allow sorting or filtering according to the similarity metric or other similarity indicator.

Figure 5:
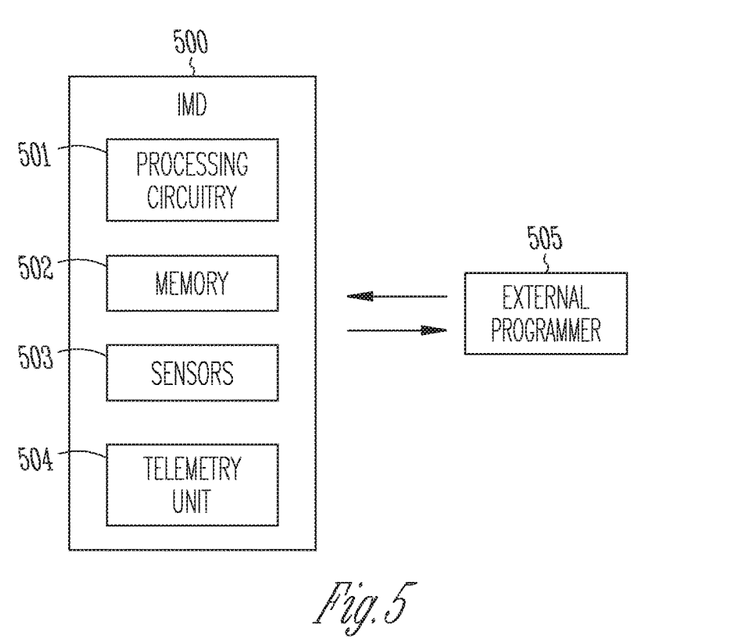
FIG. 5 illustrates a computing device such as an implantable medical device (IMD) for performing the procedures described herein in accordance with some embodiments

In another embodiment, the computing device for data classification and alert procedures is incorporated into an implantable medical device such as a cardiac rhythm management device or other implantable medical device (IMD) 500 illustrated by FIG. 5. The data classification and alert procedures may carried out entirely by the processing circuitry 501 and memory 502 of the device 500 using data collected from sensors 503 such as cardiac electrograms. The device 500 may then issue alerts when necessary via telemetry unit 504 to a server such as the computing platform 400. In another embodiment, the data classification processing (e.g., computation of classification clusters from collected data) may be performed by an external device such as external programmer 505 or platform 400, from data downloaded from the device 500. The classification cluster centroids so computed may then be communicated to the device 500 and used in issuing alerts as future data is collected.

It should be appreciated that the classification procedures described herein enable improved performance by the computing platform 400 or the computing device incorporated into the implantable medical device 400. Such improved performance in this context may include more accurate classification of clinical episode data, increased speed in classifying data, fewer false positives and fewer false negatives in issuing alerts, and lower power consumption.

Figure 6:
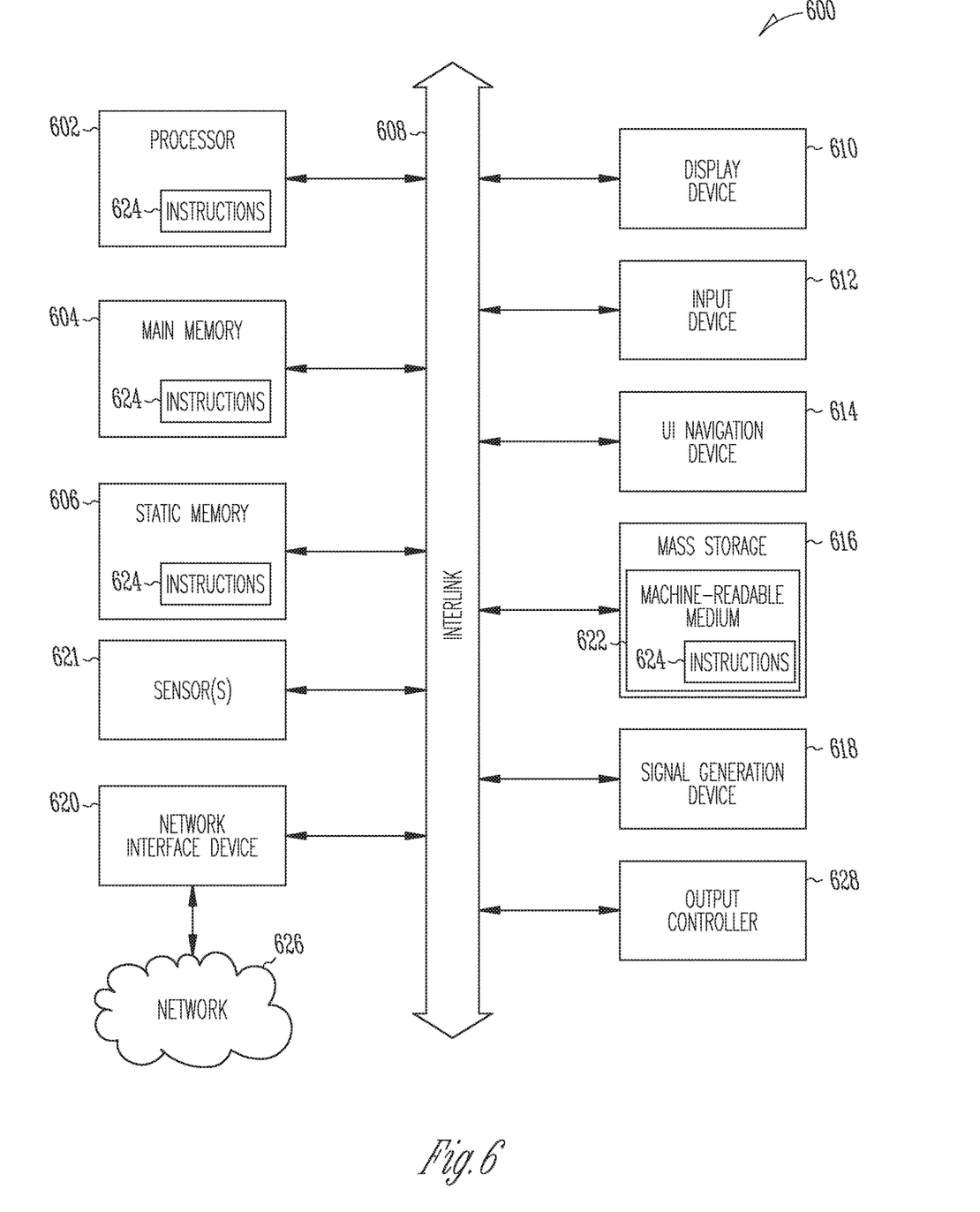
FIG. 6 illustrates a block diagram of an example machine upon which any one or more of the techniques (e.g., methodologies) discussed herein may perform.

FIG. 6 illustrates a block diagram of an example machine 600 upon which any one or more of the techniques (e.g., methodologies) discussed herein may perform. Portions of this description may apply to the computing framework of various portions of the computing platform or device, the IMD, or the external programmer.

In alternative embodiments, the machine 600 may operate as a standalone device or may be connected (e.g., networked) to other machines. In a networked deployment, the machine 600 may operate in the capacity of a server machine, a client machine, or both in server-client network environments. In an example, the machine 600 may act as a peer machine in peer-to-peer (P2P) (or other distributed) network environment. The machine 600 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Examples, as described herein, may include, or may operate by, logic or a number of components, or mechanisms. Circuit sets are a collection of circuits implemented in tangible entities that include hardware (e.g., simple circuits, gates, logic, etc.). Circuit set membership may be flexible over time and underlying hardware variability. Circuit sets include members that may, alone or in combination, perform specified operations when operating. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

Machine (e.g., computer system) 600 may include a hardware processor 602 (e.g., a central processing unit (CPU), a graphics processing unit (GPU), a hardware processor core, or any combination thereof), a main memory 604 and a static memory 606, some or all of which may communicate with each other via an interlink (e.g., bus) 608. The machine 600 may further include a display unit 610 (e.g., a raster display, vector display, holographic display, etc.), an alphanumeric input device 612 (e.g., a keyboard), and a user interface (UI) navigation device 614 (e.g., a mouse). In an example, the display unit 610, input device 612 and UI navigation device 614 may be a touch screen display. The machine 600 may additionally include a storage device (e.g., drive unit) 616, a signal generation device 618 (e.g., a speaker), a network interface device 620, and one or more sensors 621, such as a global positioning system (GPS) sensor, compass, accelerometer, or other sensor. The machine 600 may include an output controller 628, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

The storage device 616 may include a machine readable medium 622 on which is stored one or more sets of data structures or instructions 624 (e.g., software) embodying or utilized by any one or more of the techniques or functions described herein. The instructions 624 may also reside, completely or at least partially, within the main memory 604, within static memory 606, or within the hardware processor 602 during execution thereof by the machine 600. In an example, one or any combination of the hardware processor 602, the main memory 604, the static memory 606, or the storage device 616 may constitute machine readable media.

While the machine readable medium 622 is illustrated as a single medium, the term "machine readable medium" may include a single medium or multiple media (e.g., a centralized or distributed database, and/or associated caches and servers) configured to store the one or more instructions 624.

The term "machine readable medium" may include any medium that is capable of storing, encoding, or carrying instructions for execution by the machine 600 and that cause the machine 600 to perform any one or more of the techniques of the present disclosure, or that is capable of storing, encoding or carrying data structures used by or associated with such instructions. Non-limiting machine readable medium examples may include solid-state memories, and optical and magnetic media. In an example, a massed machine readable medium comprises a machine readable medium with a plurality of particles having invariant (e.g., rest) mass. Accordingly, massed machine-readable media are not transitory propagating signals. Specific examples of massed machine readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

The instructions 624 may further be transmitted or received over a communications network 626 using a transmission medium via the network interface device 620 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as WiFi®, IEEE 802.16 family of standards known as WiMax®), IEEE 802.15.4 family of standards, peer-to-peer (P2P) networks, among others. In an example, the network interface device 620 may include one or more physical jacks (e.g., Ethernet, coaxial, or phone jacks) or one or more antennas to connect to the communications network 626. In an example, the network interface device 620 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 600, and includes digital or analog communications signals or other intangible medium to facilitate communication of such software.

Various embodiments are illustrated in the figures above. One or more features from one or more of these embodiments may be combined to form other embodiments.

Method examples described herein can be machine or computer-implemented at least in part. Some examples may include a computer-readable medium or machine-readable medium encoded with instructions operable to configure an electronic device or system to perform methods as described in the above examples. An implementation of such methods can include code, such as microcode, assembly language code, a higher-level language code, or the like. Such code can include computer readable instructions for performing various methods. The code can form portions of computer program products. Further, the code can be tangibly stored on one or more volatile or non-volatile computer-readable media during execution or at other times.

The above detailed description is intended to be illustrative, and not restrictive. The scope of the disclosure should, therefore, be determined with references to the appended claims, along with the full scope of equivalents to which such claims are entitled.

What is claimed is:

1. A computing device, comprising:
processing circuitry and memory;
wherein the processing circuitry is configured to:
accept input data relating to past clinical episodes collected from a patient over time; group the past clinical episodes into one or more classification clusters accordance with a similarity metric;
receive additional input data relating to a new clinical episode collected from the patient;
assign the new clinical episode to a classification cluster if the new clinical episode is similar to one or more of the past clinical episode contained within the classification cluster as determined the similarity metric; and,
issue an alert or display the new clinical episode on a display if the new clinical episode is not assigned to a classification cluster;
wherein past and new clinical episodes are represented by an episode vector in a p-dimensional vector space made up of p numerically valued features reflective of the patient's clinical condition, p being an integer and wherein the processing circuitry is further configured to:
apply a clustering procedure to the past episode vectors to compute clusters that groups the past episode vectors into a plurality of clusters based upon a distance metric in the p-dimensional vector space;
define the one or more classification clusters as represented by the centroids of clusters of past episode vectors generated by the clustering procedure;
assign a new episode vector representing a recent clinical episode to the classification cluster that corresponds to the centroid closest to the new episode vector if the distance from the new episode vector to the closest centroid of a classification cluster is less than a specified value;
wherein the processing circuitry is further configured to:
1) select some or all of the past episode vectors as a training set and divide the training set into a training subset and a pseudo-validation subset;
2) perform the clustering procedure on the training subset and computing an optimal number of clusters as part of the clustering procedure;
3) assign vectors of the pseudo-validation subset to the clusters of the training subset in a manner that minimizes the distance from the pseudo-validation subset vector to the centroid of the cluster to which it is assigned;
4) perform the clustering procedure on the pseudo-validation subset, wherein the number of clusters to be computed is specified to be the same as the optimal number of clusters computed as part of the clustering procedure applied to the training subset;
5) evaluate the accuracy of the clusters of the training subset to which the pseudo-validation subset vectors are assigned in classifying those vectors using the clusters computed as a result of applying the clustering procedure to the pseudo-validation subset as a ground-truth standard;
6) after re-dividing the training set into different training and pseudo-validation subsets, iteratively perform 2) through 5) a specified number of times; and,
7) select the centroids of the clusters of the training subset that are evaluated with the highest accuracy to represent the classification clusters.

2. The device of claim 1 wherein the processing circuitry is further configured to:
designate one or more of the classification clusters as clinically significant so as to warrant an alert; and,
if the new episode vector is assigned to a clinically significant classification cluster, issue an alert.

3. The device of claim 1 wherein the distance metric in the p-dimensional vector space is a Euclidean distance, a squared Euclidean distance, a Minkowski distance, a Manhattan distance, a Pearson correlation distance, a Pearson squared distance, a Chebyshev distance, or a Spearman distance.

4. The device of claim 1 wherein the processing circuitry is further configured to, if a new episode vector is not assigned to a classification cluster, classify the recent clinical episode represented by that new episode vector as dissimilar to past clinical episodes.

5. The device of claim 1 wherein the processing circuitry is further configured to issue an alert if a recent clinical episode is classified dissimilar to past clinical episodes in accordance with a specified value of the distance metric.

6. The device of claim 1 wherein the processing circuitry is further configured to, after a specified period time or after a specified number of new episode vectors have been collected, add the collected new episode vectors to the past episode vectors and re-compute the classification clusters.

7. The device of claim 1 wherein the processing circuitry is further configured to test the accuracy of the classification clusters in classifying vectors by:
selecting some or all of the past episode vectors not selected as the training set to be a test set;
assigning vectors of the test set to the classification clusters in a manner that minimizes the distance from the test set vector to the centroid of the cluster to which it is assigned;

performing the clustering procedure on the test set, wherein the number of clusters to be computed is specified to be the same as the number of classification clusters; and, evaluating the accuracy of the classification clusters to which the test vectors have been assigned in classifying the test vectors using the clusters computed by applying the clustering procedure to the test set as a ground-truth standard.

8. The device of claim 1 wherein the processing circuitry is further configured to weight newer past episode vectors more heavily than older past episode vectors in computing the classification clusters.

9. The device of claim 1 further comprising a user interface and wherein the processing circuitry is further configured to incorporate patient or clinician feedback in computing the classification clusters by assigning past clinical episode vectors to a particular classification cluster in accordance with the feedback.

10. The device of claim 1 wherein the clustering procedure is a K-means algorithm performed by:
1) assigning the past episode vectors as belonging to one of K clusters, where K is an integer, and calculating the coordinates in the p-dimensional vector space of the centroid of each of the K clusters as the average of the feature values of the past episode vectors belonging to the cluster;
2) re-assigning each of the past episode vectors to the one of the K clusters whose centroid is closest to the past episode vector;
3) calculate the coordinates of the centroid of each of the K clusters as the average of the feature values of the past episode vectors belonging to the cluster; and,
4) iteratively performing 2) through 3) until a specified termination condition is met.

11. The device of claim 10 wherein the specified termination condition is selected from: a specified number of iterations having been performed, the coordinates of the centroid of each of the K clusters not changing between iterations, and the sum of the squared distances from each past episode vector to the centroid of the cluster to which it has been assigned being below a specified threshold value.

12. The device of claim 10 wherein the processing circuitry is further configured to calculate an optimal value for the number of clusters K by:
computing clusters using the K-means clustering procedure for successively increasing values of K;
for each set clusters computed using a particular K value, computing a dispersion function defined as the sum of the squared distances between a centroid of a cluster and the vectors belonging to the cluster summed over all of the clusters in the set; and,
selecting the optimal value of K as the K value when the marginal decrease in the dispersion function as K is increased is maximized.

13. The device of claim 1 wherein the accuracy of clusters in classifying vectors is evaluated as being positively related to a mutual information MI between the set of clusters to be evaluated {w(1), w(2), . . . w(N) and the set of clusters regarded as ground truth {c(1), c(2), . . . c(N)}, where w(k) is the set of vectors in cluster k of the set of clusters to be evaluated, c(j) is the set of vectors in cluster j of the set clusters regarded as ground truth, N is the number of clusters in the set of clusters to be evaluated and the set of clusters regarded as ground truth, and wherein MI is calculated as:

$$MI = \sum_k^N \sum_j^N P(w(k) \cap c(j)) \log \frac{P(w(k) \cap c(j))}{P(w(k))P(c(k))}$$

where $P(w(k))$, $P(c(j))$, and $P(w(k) \cap c(j))$ are the probabilities of a vector being $w(k)$, $c(j)$, and the intersection of $w(k)$ and $c(j)$, respectively, estimated as the relative frequencies of the vectors in the clusters to be evaluated and the clusters regarded as ground truth.

14. A computer-implemented method comprising:
accepting input data relating to past clinical episodes collected from a patient over time;
grouping the past clinical episodes into one or more classification clusters accordance with a similarity metric;
receiving additional input data relating to a new clinical episode collected from the patient;
assigning the new clinical episode to a classification cluster if the new clinical episode is similar to one or more of the past clinical episode contained within the classification cluster as determined the similarity metric; and,
issuing an alert or displaying the new clinical episode on a display if the new clinical episode is not assigned to a classification cluster;
wherein each past clinical episode is represented by a past episode vector in a p-dimensional vector space made up of p numerically valued features reflective of the patient's clinical condition, p being an integer;
applying a clustering procedure to the past episode vectors to compute clusters that groups the past episode vectors into a plurality of clusters based upon a distance metric in the p-dimensional vector space;
defining the one or more classification clusters as represented by the centroids of clusters of past episode vectors generated by the clustering procedure;
assigning a new episode vector representing a recent clinical episode to the classification cluster that corresponds to the centroid closest to the new episode vector if the distance from the new episode vector to the closest centroid of a classification cluster is less than a specified value; and further comprising:
1) selecting some or all of the past episode vectors as a training set and dividing the training set into a training subset and a pseudo-validation subset;
2) performing the clustering procedure on the training subset and computing an optimal number of clusters as part of the clustering procedure;
3) assigning vectors of the pseudo-validation subset to the clusters of the training subset in a manner that minimizes the distance from the pseudo-validation subset vector to the centroid of the cluster to which it is assigned;
4) performing the clustering procedure on the pseudo-validation subset, wherein the number of clusters to be computed is specified to be the same as the optimal number of clusters computed as part of the clustering procedure applied to the training subset;
5) evaluating the accuracy of the clusters of the training subset to which the pseudo-validation subset vectors are assigned in classifying those vectors using the clusters computed as a result of applying the clustering procedure to the pseudo-validation subset as a ground-truth standard;

6) after re-dividing the training set into different training and pseudo-validation subsets, iteratively performing 2) through 5) a specified number of times; and, 7) selecting the centroids of the clusters of the training subset that are evaluated with the highest accuracy to represent the classification clusters.

15. The method of claim 14 further comprising: after a specified period time or after a specified number of new episode vectors have been collected, add the collected new episode vectors to the past episode vectors and re-compute the classification clusters.

16. The method of claim 14 further comprising testing the accuracy of the classification clusters in classifying vectors by:

selecting some or all of the past episode vectors not selected as the training set to be a test set;

assigning vectors of the test set to the classification clusters in a manner that minimizes the distance from the test set vector to the centroid of the cluster to which it is assigned;

performing the clustering procedure on the test set, wherein the number of clusters to be computed is specified to be the same as the number of classification clusters; and, evaluating the accuracy of the classification clusters to which the test vectors have been assigned in classifying the test vectors using the clusters computed by applying the clustering procedure to the test set as a ground-truth standard.

17. The method of claim 14 wherein the clustering procedure is a K-means algorithm performed by:

1) assigning the past episode vectors as belonging to one of K clusters, where K is an integer, and calculating the coordinates in the p-dimensional vector space of the centroid of each of the K clusters as the average of the feature values of the past episode vectors belonging to the cluster;

2) re-assigning each of the past episode vectors to the one of the K clusters whose centroid is closest to the past episode vector;

3) calculate the coordinates of the centroid of each of the K clusters as the average of the feature values of the past episode vectors belonging to the cluster; and, 4) iteratively performing 2) through 3) until a specified termination condition is met.

* * * * *